United States Patent [19]

Landi et al.

[11] Patent Number: 5,212,720
[45] Date of Patent: May 18, 1993

[54] DUAL RADIATION TARGETING SYSTEM

[75] Inventors: Michael K. Landi, Snyder; Robert M. Lifeso, East Amherst, both of N.Y.

[73] Assignee: Research Foundation-State University of N.Y., Buffalo, N.Y.

[21] Appl. No.: 827,672

[22] Filed: Jan. 29, 1992

[51] Int. Cl.$^5$ ............................................. A61B 6/08
[52] U.S. Cl. ...................................... 378/206; 378/205; 378/164; 33/262
[58] Field of Search ............... 378/205, 206, 207, 163, 378/164; 33/262

[56] References Cited

U.S. PATENT DOCUMENTS

| | | | |
|---|---|---|---|
| 3,628,021 | 12/1971 | MacDonald | 378/147 |
| 3,629,594 | 12/1971 | Sandberg | 378/95 |
| 4,117,337 | 9/1978 | Staats | 378/17 |
| 4,167,675 | 9/1979 | Stodberg | 378/153 |
| 4,296,329 | 10/1981 | Mirabella | 378/18 |
| 4,356,400 | 10/1982 | Polizzi | 378/138 |
| 4,406,015 | 9/1983 | Koga | 378/50 |
| 4,426,726 | 1/1984 | Cheetham | 378/206 |
| 4,521,905 | 1/1985 | Hosokawa | 378/206 |
| 4,578,806 | 3/1986 | Grass | 378/162 |
| 4,836,671 | 6/1989 | Bautista | 378/206 |
| 5,013,317 | 5/1991 | Cole et al. | 378/205 |
| 5,031,203 | 7/1991 | Trecha | 378/205 |

FOREIGN PATENT DOCUMENTS 3803566  8/1989  Fed. Rep. of Germany.
2175578A  12/1986  United Kingdom.

OTHER PUBLICATIONS

Laser Mech Product Sheets Dates 1990—2 Sheets.

Primary Examiner—David P. Porta
Assistant Examiner—Kim-Kwok Chu
Attorney, Agent, or Firm—M. Lukacher; Kathleen Terry

[57] ABSTRACT

Subsurface regions of an X-ray transparent but optically opaque object are targeted along a visible line of sight obtained by the use of two radiation sources (an X-ray and light beam source, preferably a laser). The central ray from the X-ray source and the light beam are aligned using a calibration fixture, one to the other and both with respect to structures internal to the object being imaged to provide the visible line of sight. The system (method and apparatus) may be used in surgical applications for selective illumination and sighting to reach specific subsurface members of a patients anatomy by guiding an incision.

18 Claims, 8 Drawing Sheets

DUAL RADIATION TARGETING SYSTEM

DESCRIPTION

1. Field of the Invention

This invention pertains to a system (method and apparatus) for aligning a first radiation source, (especially an X-ray source), with a beam from a second radiation source, (especially a laser), whereby structures internal to an object imaged with the first radiation can be located using the beam of second radiation.

The system is especially suitable for use in surgery for locating specific sub-surface regions of the anatomy and providing a light beam for sighting an incision so that the specific region can be reached and exposed for surgical operations thereon. The invention will also be found useful for precisely locating other internal structures, such as a region of an encased electronic circuit board or integrated circuit computer chip.

Another use for the invention is to allow for the accurate location and positioning on the surface anatomy corresponding to internal radiation emanating from radioactive sites within the patient produced by radionuclides. Examples include tumor marking, by means of injected radioactive substances which preferentially localize in specific areas of the body which indicate pathologic conditions. These areas may require surgical intervention, in which case the advantage, of knowing surface location and true access of approach to the pathologic site, lies in the potential for surgical trauma in accessing the tumor or other pathologic state.

2. Description of the Prior Art

The use of lasers in conjunction with imaging systems has, to a limited extent, been heretofore contemplated. In Staats, U.S. Pat. No. 4,117,337, issued Sep. 26, 1978, an arrangement is described for placing the area of the patients anatomy to be analyzed in a fixed relation to the scanning heads of the X-ray machinery. Having been thus positioned, the table on which the patient has been placed moves a preset distance in the direction of the scanning heads, at which time the area on the patient to be analyzed has the same geometric relation to the scanning head that it formerly had to the laser system. This imaging system permits the precise visualization of internal structures in the patients anatomy, which may later be the subject of surgical procedures. However, when it comes time to operate on the patient, the only indication the surgeon has as to how to access the internal structure is a radiograph of the internal structures, which does not provide an accurate means of approach. Therefore the surgeon must, in accessing the internal structure, rely on his knowledge of general anatomical features in the patient population at large, including the variability that exists therein. This means that precise location of points on the surface of the patient which provide the most direct access to internal structures is not possible.

Polizzi et al. U.S. Pat. No. 4,356,400, issued Oct. 26, 1982, discloses a method and device for setting up floor or wall mounted cassette holders with respect to an X-ray source. In the procedure disclosed a cylindrical central ray locating device is placed on the X-ray source housing so as to occlude all X-rays except the central ray and those that are slightly angulated thereto. Alignment of the central ray and the bore of the cylindrical device is achieved by observing the behavior of a phosphorized indicator on the end of the device. This central ray locating tool may require the exposure of a technician to X-rays during the first stage of setup and the tool cannot be used during imaging diagnostic procedures because it occludes the broad X-ray beam that is required for imaging. The second stage of setup, involves the removal of the above mentioned cylindrical central ray locating device, and the substitution of a cylinder containing a laser with the attendant possibility of a change in the mounting alignment and therefore an error in the representation of the central ray by the laser. From a surgical perspective, the above mentioned laser can not be used while imaging internal structures because its placement in the path of the X-ray beam obstructs the image forming rays.

British Pat. No. GB 2175778A published Dec. 3, 1986, discloses a device for aligning a patient at the proper distance from a fixed X-ray source so as to allow for a properly focused image to be formed on a photographic plate. A beam splitter and a mirror are used to create converging primary and a secondary laser beams which intersect at a predetermined distance from the X-ray source. The device aligns the patient at the proper film to focus distance. There are deviations in the central X-ray beam due to normal anode wear on the X-ray source and concomitant deviation of the X-ray path from the source. It is not possible to use this device to accurately correlate the point on the patient as illuminated by the laser with an imaged point of the patient's internal anatomical structure. There is no method for verifying that the path of the laser is colinear with an given path of a ray emanating from the X-ray source in the direction of the target. In addition the above mentioned patent does not disclose any method for correlating the image produced by the X-ray device with the visual image indicated by the laser.

The following patents also involve devices using X-rays and light beams for various purposes: MacDonald U.S. Pat. No. 3,628,021, Dec. 14, 1971; Sandberg U.S. Pat. No. 3,629,524, Dec. 21, 1971; Mirabella U.S. Pat. No. 4,296,329, Oct. 20, 1981; Koga U.S. Pat. No. 4,406,015, Sep. 20, 1983; Stodberg U.S. Pat. No. 4,167,675, Sep. 11, 1979; Cheetham U.S. Pat. No. 4,426,726, Jan. 17, 1984; Hosokawa U.S. Pat. No. 4,521,905, Jan. 4, 1985; Grass U.S. Pat. No. 4,578,806, Mar. 25, 1986; and German patent publication DE No. 3,803,566, Aug. 24, 1989.

All of the foregoing approaches have one common failing and therefore fail to meet a long felt need, which is to accurately locate a subsurface region of the patient's anatomy and guide incisions to an operating site both simultaneously, without unnecessary exposure to either the patient or the surgeon to ionizing radiation (X-rays).

SUMMARY

It is therefore the principal object of the invention to provide an improved system for accurate location of a position on the patient's surface anatomy that corresponds to, and provides a true access of approach to, an imaged subsurface or deep structure imaged by an external radiation source. A deep structure is, for example, a portion of the internal anatomy of a patient which is identifiable from surrounding structures by its differential radiotranslucency and which is medically of interest, e.g. a tumor, or a locking screw hole in femoral rod or metal plate.

An ancillary object of the invention is to provide an improved laser surgery system which reduces the inherent error in surgery using hand held lasers, by deep structure targeting. The invention enables the use of operative high power lasers to increase the accuracy, and provide direct access of approach to subsurface structures which need to be cauterized, vaporized, excised or coagulated, without the attendant surgical trauma, which is the result of current use of hand held surgical lasers.

A still further object of the invention is to provide an improved system for surgical operations which allows for automation of such operations, which involve the use of a surgical laser scalpel through computer controlled positioning of the surgical laser, and is especially adapted for use in microsurgery on deep structures as in the inner ear or on photosensitive tumors.

Briefly described, a system in accordance with the invention provides accurate access of approach to a desired deep structure visualized with a medical or other imaging system. A fixture is mounted in the path of the first radiation source, for example the X-ray source of a fluoroscope. The fixture removably mounts a calibration tube. A second radiation source, for example, a laser providing a light beam, is also mounted in the fixture. The light beam is directed by means of a mirror which is transparent to the first radiation, for example, an X-ray transparent mirror, along the axis of the calibrating tube. This beam is in general, any reflected portion of the second radiation. Radio opaque cross hairs at opposite ends of the calibrating tube are visualized on the fluoroscope's TV monitor, which has a detector sensitive to the radiation from the first source (X-rays) and provides an image which is illuminated by that radiation. The fixture has means for adjusting the X, Y coordinates of the light beam with respect to a central ray of the first radiation (X-rays) so that the ray and beam are aligned along a line through the intersections of the cross hairs of the calibration tube. Then, the cross hairs are, when viewed on the TV monitor, superimposed on one another, which indicates that the line running from the intersections of the cross hairs is collinear with the central ray. The ray is preferably the central ray, but may be another ray and is hereafter called an identifiable ray. Due to the precise alignment of the reflected portion of the secondary radiation with the cross hairs of the calibration tube the reflected portion of the secondary radiation is colinear with the calibration tube and with the identifiable ray from the X-ray source. At the point indicated by the reflected portion of the secondary radiation on the first radiation image forming detector, a radio-opaque target symbol is affixed. The target symbol is now collinear with the identifiable ray and the reflected portion of the secondary radiation; i.e., the central X-ray and the light beam are aligned with the target. When the X-ray source is turned off, the light beam provides a visible line of sight to the deep structure which is located between the X-ray source and the target. The fixture does not obstruct the first radiation and the secondary radiation can, therefore, operate concurrently with the first radiation for locating the deep structure and providing the visible line of sight thereto.

Any object placed in the path of the identifiable ray will be imaged by the first and second radiation source both internally and externally in a manner which allows superposition of the images.

Surgical and other invasive procedures using X-rays, including laser assisted location of deep structures and automatic laser assisted surgery on deep structures may be performed in accordance with the invention.

BRIEF DESCRIPTION OF DRAWINGS

The foregoing and other objects, advantages and features of the invention will become more apparent from the following detailed description taken in conjunction with the drawings in which.

DETAILED DESCRIPTION

Figure 4:
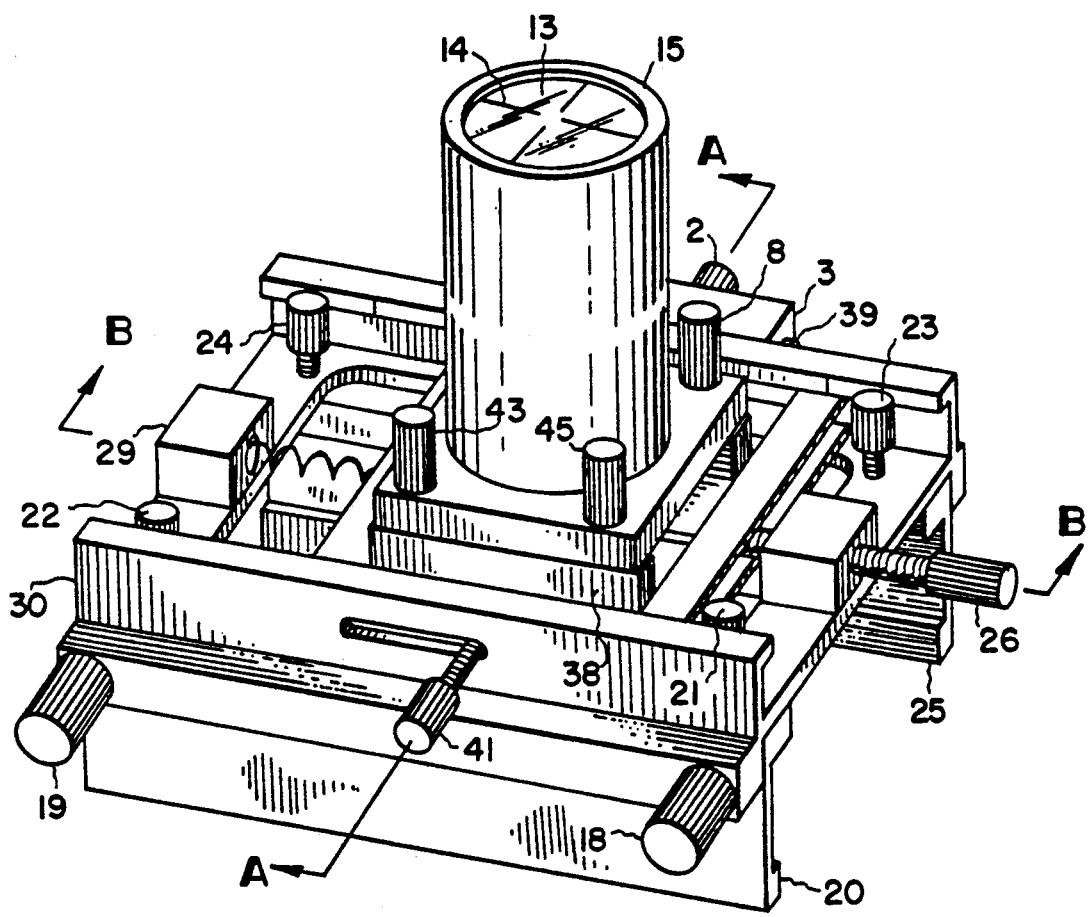
FIG. 4 is a perspective view of the X-Y-Z positioner with calibration tube in place, the view being rotated 90° counter-clockwise from the view of FIG. 3.
Figure 5:
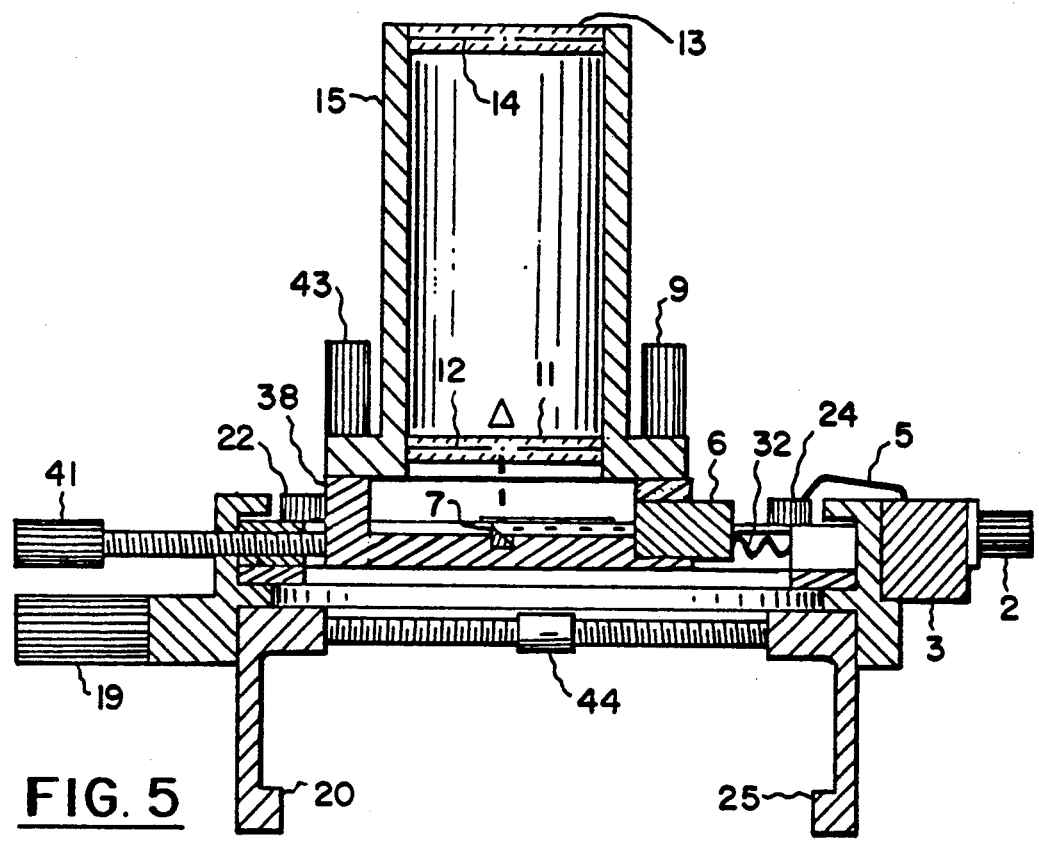
FIG. 5 is a sectional view along the line A—A in FIG. 4.
Figure 6:
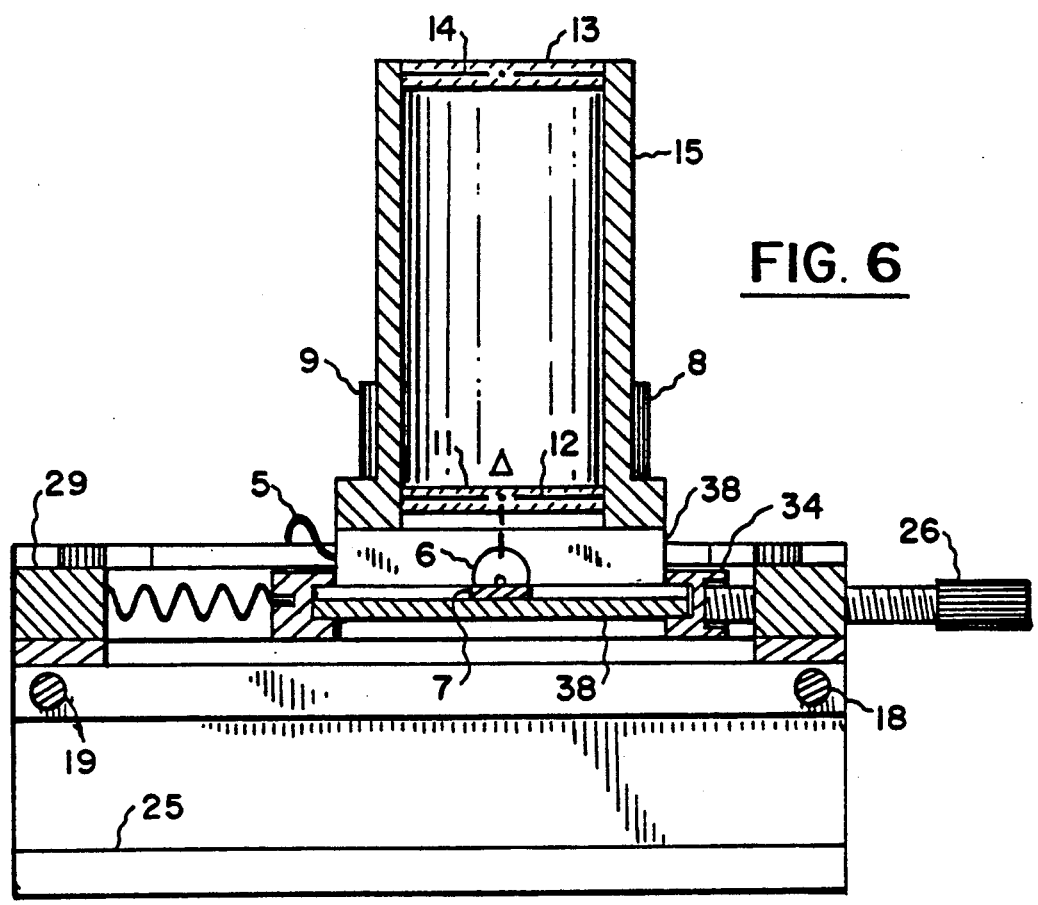
FIG. 6 is a sectional view taken along the line B—B in FIG. 4.
Figure 7:
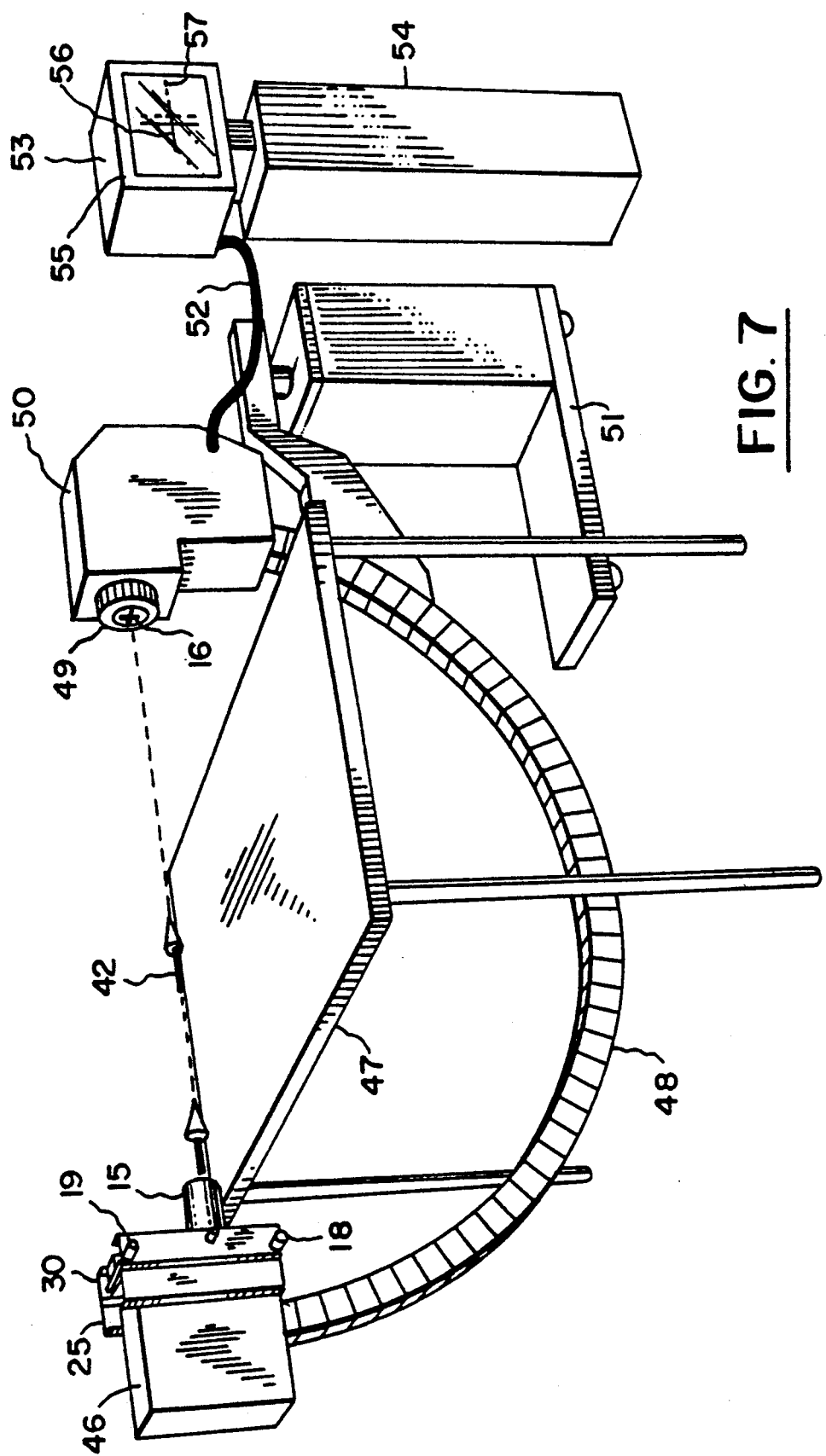
FIG. 7 is a perspective view of the system including an X-ray fluoroscope.

The illustrative dual radiation targeting apparatus in FIG. 4 comprises a framework which consists of a base 30 and a clamping mechanism, 18, 19, 20, and 25 which are mounted, as shown in FIG. 7 on the X-ray source 46 of a fluoroscope 51 consisting of X ray source 46, held in fixed relation to an image intensifier 49, within housing 50, by generally C shaped yoke or arm 48. Mounting is performed by turning clamping screws 18, 19 having reverse threaded portions 44 thereon, shown in FIG. 5, such that clamp arms 20, 25 are drawn together to affix the above mentioned assembly to the X-ray source 46. Adjustment screws 21, 22, 23, 24 are turned to make the base 30 orthogonal to the axis between the X-ray source 46 and the image intensifier 49, which provides a detector of the image formed by X-ray illumination from the source 46.

As shown in FIG. 7, the fluoroscope 51 is energized and an image is viewed on screen 55 of monitor 53 on stand 54. The image consists of cross hairs 56, 57 which represent the radio-opaque (opaque to X-rays, radiation from a radioactive source or the like) cross hairs 12, 14 shown in FIG. 1., which lie generally in the path of radiation sources 1 or 46 in FIG. 7. These cross hairs 12, 14 are contained in radiolucent disks 11, 13 which are in turn mounted in the bore of calibration tube 15 which is permanently fixed to calibration tube base 10, which is removably affixed by means of locking screws 8, 9, 43, 45 as shown in FIG. 1 and FIG. 4, to the radiolucent X stage 38.

Figure 2:
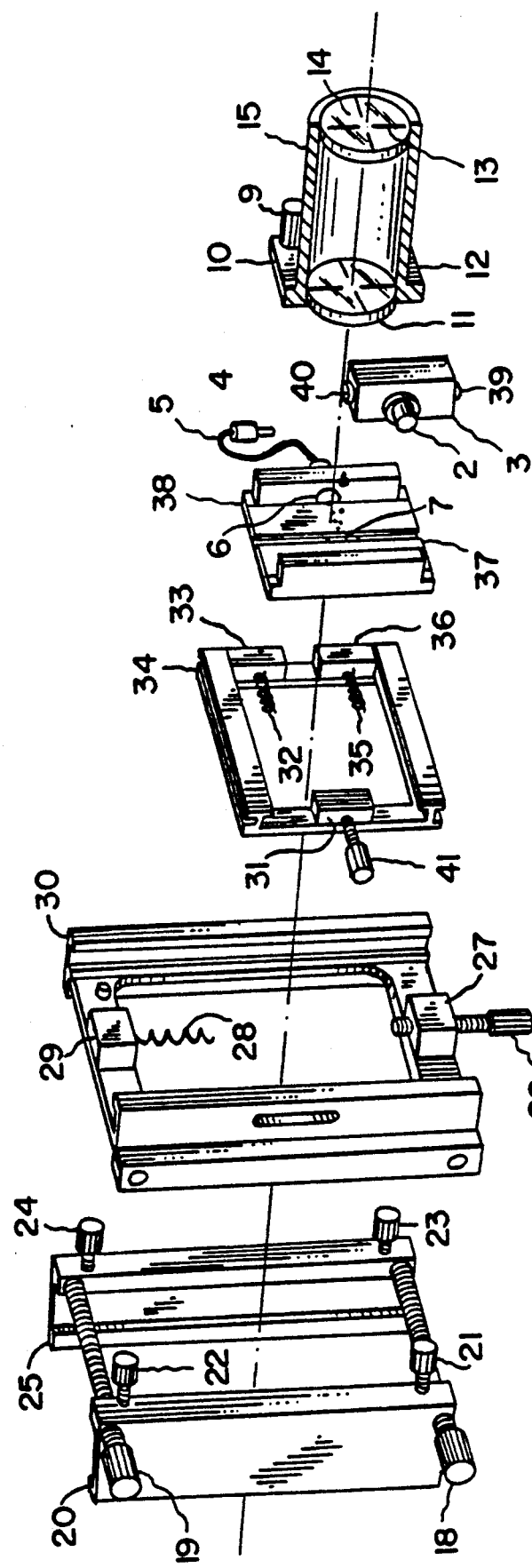
FIG. 2 is an exploded view of an X-Y-Z positioner and calibration tube of the exemplary system.

As shown in FIG. 2; the radiolucent X stage 38 and its associated adjustment mechanism 31, 32, 33, 35, 36, 41; the Y stage 34; the laser 6, and the radiolucent mirror 7, all comprise a fixture. In a preferred embodiment the laser source is a laser diode which emits a visible beam 42 shown in FIG. 7. The radiolucent X stage 38 is slidably affixed within the Y stage 34 and is positioned therein by means of the cooperative relationship of X axis screw 41 and its receptacle 31 and return springs 32, 35 and their respective receptacles 33, 36. The slidable relationship of the Y stage 34 with respect to base 30 is facilitated by slot 63 shown in FIG. 3. Receptacles 31, 33, 36 are permanently affixed to Y stage 34. The Y-stage 34 is in turn slidably affixed within base 30 and is positioned therein by means of the cooperative relationship of Y axis screw 26 and its receptacle 27 and return spring 28 and its receptacle 29 which receptacles 27, 29 are permanently affixed to base 30.

A calibration procedure is then performed, the object of which is to adjust the position of the X, Y stages 38, 34 to move the calibration tube 15 and cross hairs 12, 14 so as to align the cross hair images 56, 57 on screen 55 in FIG. 7 such that they are superimposed. This will indicate that the center axis of the calibration tube cross hairs is colinear with an axis of radiation and hence an identifiable ray.

Figure 1:
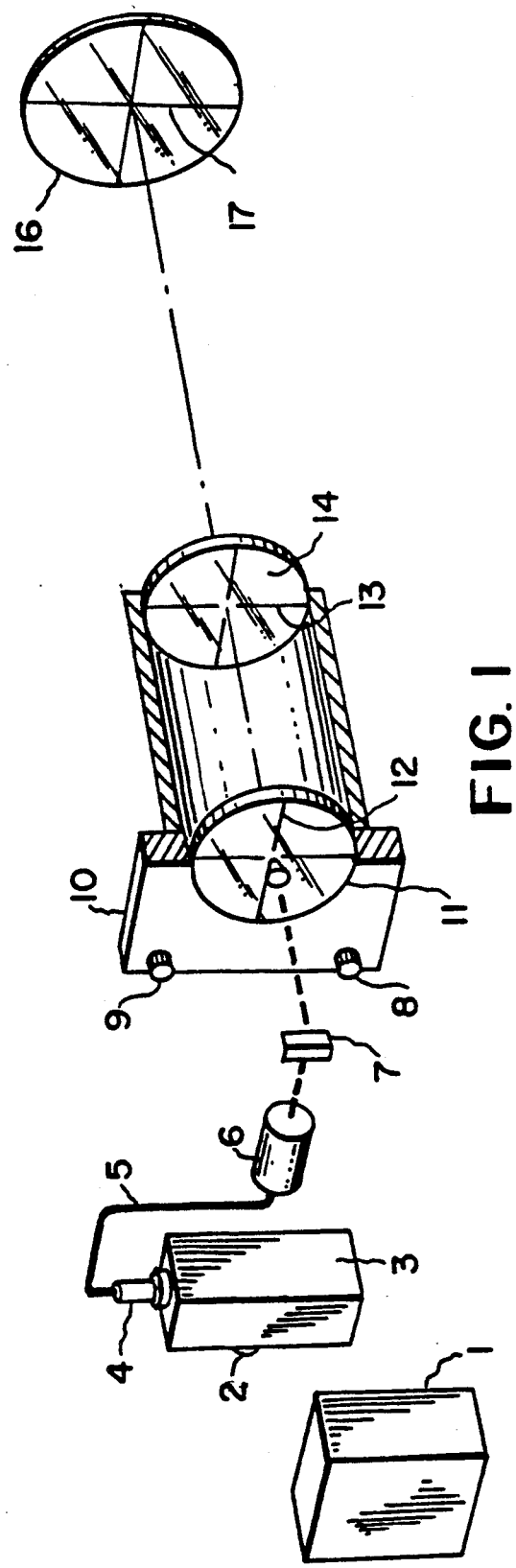
FIG. 1 is a diagrammatic, exploded, perspective view showing generally the light and X-ray radiation sources, the calibration tube and the target of an exemplary system in accordance with the invention.

As shown in FIGS. 1 and 2, laser 6 is mounted in radiolucent X stage 38 so as not to occlude the radiation from the X-ray sources 1 or 46, in FIG. 7. Laser 6 is mounted in radiolucent X stage 38 so as to direct its beam at radiolucent mirror 7 mounted in slot 37 in radiolucent X stage 38. The cooperative relation of laser 6 and mirror 7 is such that the reflected laser beam, the beam reflected off the mirror 7, follows a path which is colinear with the axis that passes through the centers of calibration tube cross hairs 12, 14. Power is supplied to the laser by means of a rechargeable power pack 3 which power pack has a control switch 2, a recharging receptacle 39, and a laser power output receptacle 40. Laser power plug 4 transmits power to the laser via wire bundle 5.

As indicated in FIG. 7, collinearity between an identifiable ray and the laser beam 42 having been established, the next procedural step is to adhesively place translucent target disk 16 on image intensifier screen 49 so that the target symbol, or in this case the radio-opaque cross hairs 17, is positioned so that the target symbol center intersects the laser beam 42.

The installation and calibration procedure having been completed, the calibration cross hairs 12, 14, and the target symbol cross hair 17 will when viewed on TV screen 55 appear as a single cross hair. This indicates that the laser beam and the target symbol are collinear with the identifiable ray and that the calibration tube can be removed if desired to increase the operating distance between the dual radiation targeting apparatus mounted on the X-ray source 46 and the image intensifier 49. This removal is accomplished by means of loosening locking screws 8, 9, 43, 45. It is preferable, however, that the fluoroscope be recalibrated as mentioned above, before each procedural use of the fluoroscope in order to ensure that the deviations of the identifiable ray that take place as a result of electrode wear in the X-ray source 46 do not disrupt the collinearity of the reflected laser beam 42 and the target symbol 17.

Figure 8:
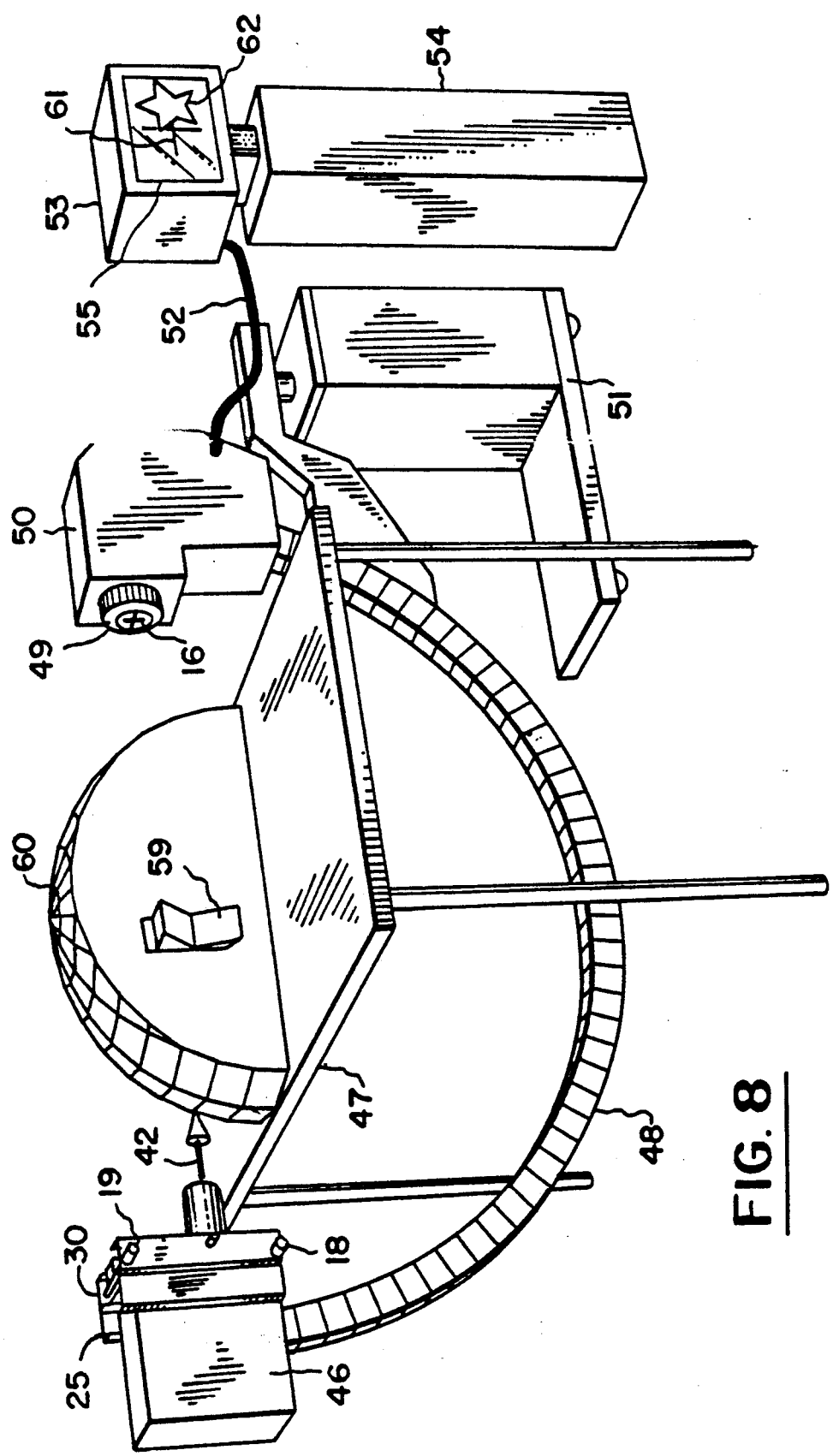
FIG. 8 is a perspective view of the system in operation in locating a deep structure.

The advantages of the above mentioned procedure will be readily apparent by reference to FIG. 8 in which star 59 represents a deep structure, for example: a hole in a radio-opaque intramedullary rod reinforcing a fractured femur, and requiring a screw to be placed through the surrounding femur and into the hole in said intramedullary rod in order to permanently secure the position of the intramedullary rod in the femur. Hemisphere 60, on surgical platform 47, represents the surrounding bone and tissues all of which have varying degrees of radiolucency.

The image of the radio-opaque intramedullary rod and the locking screw hole represented as the star's center 62, and the target symbol 61 are viewed on the TV screen 55. Fluoroscope 51 position adjustments are made so as to place the center of the target symbol 61 over the center of the hole in the intramedullary rod 62. Having secured the position of the patient and the fluoroscope in the above mentioned relationship, the fluoroscope may be de-energized if desired, since the laser beam provides a visible line of sight and indicates the axis of approach to and the location of the deep structure of interest, in this case the intramedullary rod hole. The surgeon may now surgically approach the femur and drill through it with full confidence that, as long as he tip of the drill follows the line of sight provided by the laser beam 42, the drill will directly access the hole. There has been a long felt need for this method and apparatus, as indicated by the following complications currently associated with intramedullary rod placement. Current technique requires repeated fluoroscopic images to obtain position information, with concurrent ionizing radiation exposure of both the patient and surgeon. The trial and error of the current technique results in excessive time under anesthesia and results in misplaced holes and weakening of the femur resulting in post operative secondary fractures. The subject invention however allows accurate and rapid placement of screws in the intramedullary rod, which in turn effectively reduces complications due to screw placement, time under anesthesia, cumulative ionizing radiation exposure of the patient and the surgeon.

Figure 9:
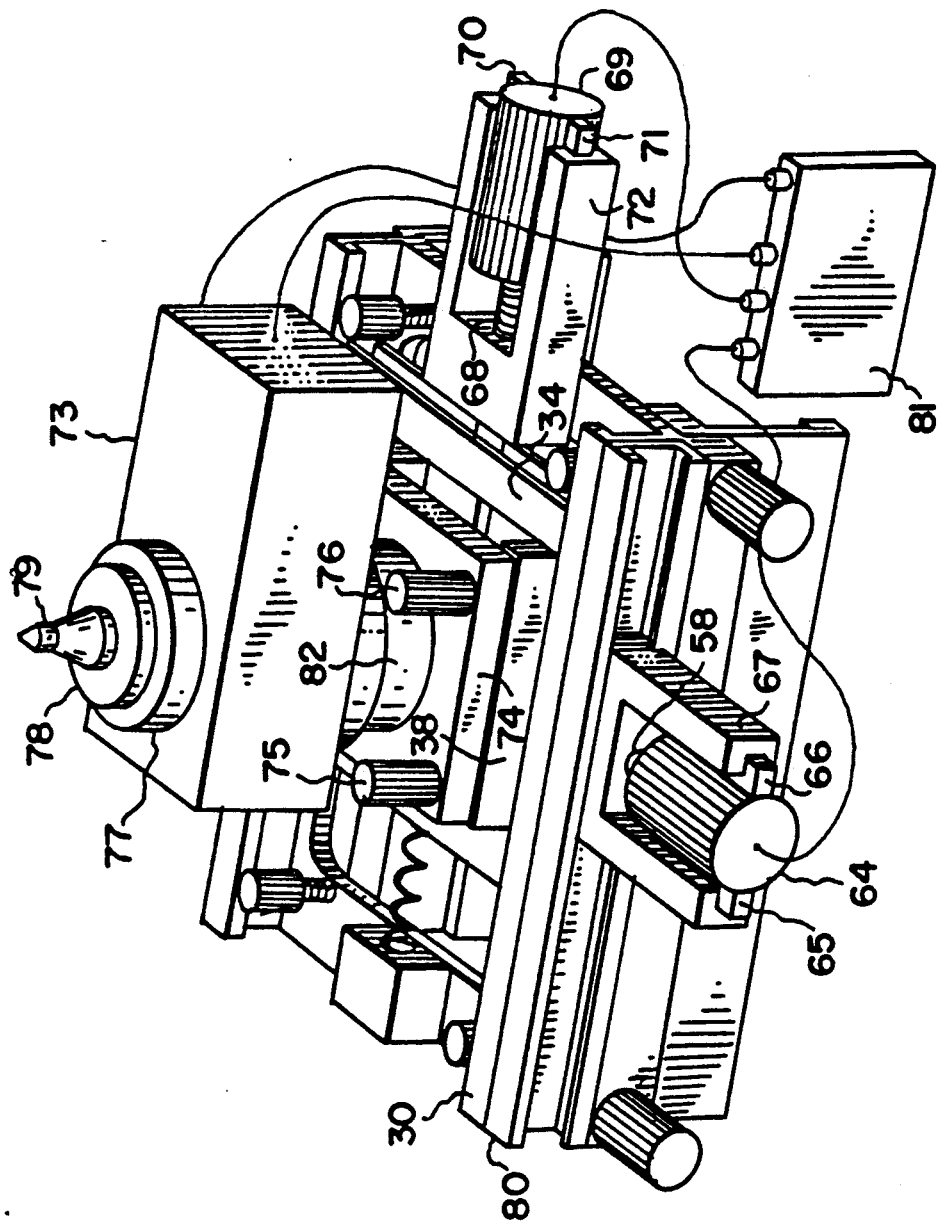
FIG. 9 is a perspective view similar to FIG. 4 showing a surgical laser and means for the automatic positioning thereof.

In accordance with another embodiment of the invention shown in FIG. 9, the calibration controls are automatic and a surgical laser, for example, a $CO_2$ laser is used in place of the laser diode, in order to cut, cauterize, coagulate, or vaporize, an imaged structure. Furthermore, it may be advantageous to program a path for the surgical laser so as to extend the above mentioned functions to instances in which a boundary, an area, rather than a hole, is desired to be cut, cauterized, coagulated, vaporized or excised.

Referring to FIG. 9, servo-motors 64, 69 position the X and Y stages during calibration and programmed operation. X servo-motor 64 is attached to shaft 58, which corresponds in function to shaft 41 in FIG. 2,3,4,5. X servo-motor 64 is slidably mounted in frame 67 by means of slides 65, 66 so as to allow for motor displacement corresponding to X-stage 38 displacement during calibration and programmed operation. In addition, frame 67 is slidably mounted in slide rail 80, which slide rail is permanently affixed to base 30, so as to also allow for displacement of frame 67 and motor 64 corresponding to displacement of Y stage 34. Y servo-motor 69 is attached to shaft 68, which corresponds in function to shaft 26 in FIGS. 2,3,4,5. Y servo-motor 69 is slidably mounted in frame 72 by means of slides 70, 71 so as to allow for motor displacement corresponding to Y-stage 34 displacement during calibration and programmed operation.

Figure 3:
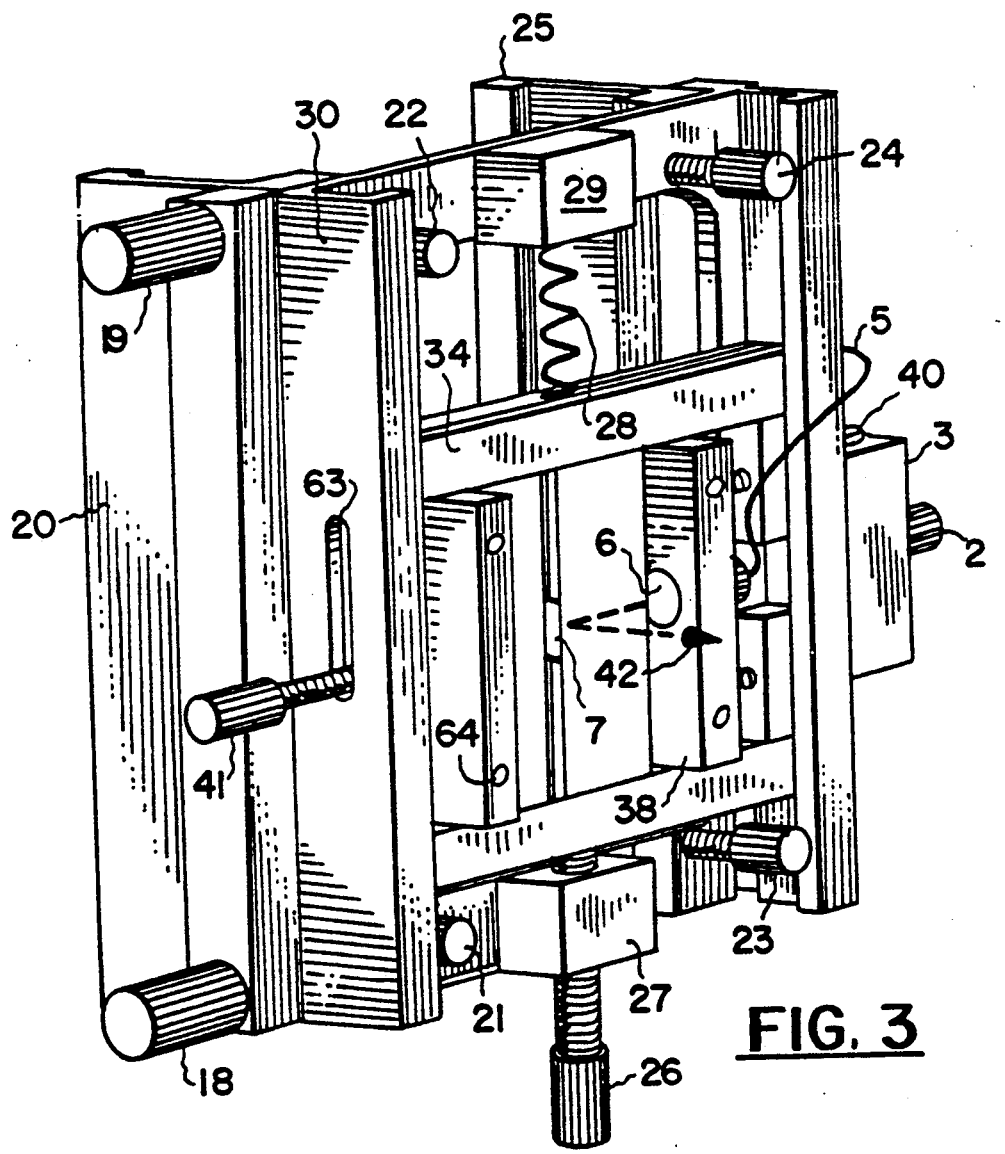
FIG. 3 is a perspective view of the X-Y-Z positioner without calibration tube.

Following the calibration procedure outlined in the first preferred embodiment above, the calibration tube 15 and attached base 10 shown in FIG. 4, will be removed as shown in FIG. 3. A $CO_2$ laser is substituted for the laser diode 6 and a mirror suitable for reflecting the $CO_2$ laser beam is installed so as to direct the $CO_2$ laser beam along the same path as the reflected beam from the laser diode.

As shown in FIG. 9 an autofocus system with Z axis drive 73 is mounted in the same manner and in the same location as the calibration tube base. Autofocus system with Z axis drive, may notably be an apparatus such as that sold under the trademark ACCUFOCUS by the Laser Mech Company, Southfield Mich., 48037-2064. The autofocus system contains a Z-axis servomotor drive in housing 73, a focusing tip 79, a high pressure jet manifold 78, a large aperture lens manifold 77 and a path enclosure 82. The autofocus system is attached to X stage 38 by means of base plate 74 and associated mounting screws, of which two are shown, 75 and 76. As shown in FIG. 9 the control wires for energizing the laser 6 as well as the three servomotors 64, 69, 73 are attached to a control box 81. The programming and control of the servo-motors 73, 69, 64 can be accomplished by many means ranging from manual to automatic. In the manual mode each axis of motion of the $CO_2$ laser would be under human control by means of switches and associated control circuitry which known in the prior art. In he automatic mode, the X, Y, Z coordinates of a deep structure imaged on screen 55 are downloaded into a computer by means of the interaction of a light pen held by a surgeon and a digitizing grid superimposed on screen 55 the interaction of which allows for downloading path coordinates into the computer. These coordinates are, after mounting of the surgical laser, used to control the area excised by the surgical laser, in a manner corresponding to the light pen tracings made by the surgeon.

We claim:

1. A dual radiation imaging and targeting system comprising fluoroscopic imaging means having a first source of radiation and means including a detector for providing an image of an object positioned between said first source and said detector by radiation which illuminates and is transmitted through said object, said radiation extending along a path between said source and said detector, a fixture attachable to the first source and intersecting of said path, said fixture including means incrementally movable and positionable along two axes orthogonal to each other and generally orthogonal to said path, at least a portion of said fixture intersected by said path being radiolucent to the radiation from said first source, a radiolucent mirror mounted in the radiolucent portion of said fixture and being intersected by said path, a second source providing a visible beam of radiation incident on said mirror and carried by said fixture and offset from said path, said visible beam being reflected from said mirror along said path, collinearizing means removably attachable to said fixture and extending along said path, said collinearizing means including means for providing with said image providing means a visual indication of the relative alignment of the visible beam and an identifiable ray of the radiation from said first source, and a radio-opaque target symbol mountable on the detector at the point of intersection of the path and said visible beam.

2. The system of claim 1 wherein said radio-opaque target symbol is disposed at the intersection of said ray and said visible beam when they are collinear with each other.

3. The system according to claim 2 wherein said first source of radiation is an X-ray source and said second source is a laser.

4. The system according to claim 3 wherein said laser is operable at sufficient power to cut into said object.

5. The system according to claim 1 further comprising motor operated means for actuating said incrementally movable and positionable means.

6. The system according to claim 1 wherein said collinearizing means comprises a tube having means for indicating the location of said identifiable ray with respect to said path.

7. The system according to claim 6 wherein said indicating means are radio-opaque cross hairs across opposite ends of said tube aligned to intersect along the axis of said tube.

8. A dual radiation targeting apparatus operative with first radiation which emanates from a first source for imaging a deep structure internal of an object positioned along a line between said first source and a detector, which apparatus comprises a second source of visible radiation, a fixture which is substantially transparent with respect to the first radiation, said fixture being positioned along the line between said first source and on one side of the object, a mirror carried by said fixture which is reflective of said visible radiation and substantially transparent to said first radiation, calibration means including a pair of cross-hairs spaced from each other in a direction along said line, viewing means on which an image of said cross-hairs appears, means for positioning said pair of cross-hairs until the images thereof on said viewing means are superimposed thereby calibrating said apparatus so that an identifiable ray of said first radiation is transmitted along said line, said mirror being positioned along said line so that said identifiable ray of said first radiation is transmitted therethrough along said line, positioning means for moving said mirror so that a reflected portion of said visible radiation extends from said mirror along the line in a direction toward the object in collinear relationship with said identified ray, a target symbol which is at least partially opaque to said first radiation and positioned on the line between said object and the detector, whereby said structure internal to the object can be located along a line of sight defined by said reflected portion which is incident on said object and is along said line.

9. The apparatus according to claim 8 wherein said first source produces X-rays and said second source produces a laser beam.

10. A dual radiation targeting device, for use with a laser and a X-ray imaging system emitting an X-ray beam along a central axis through an object to an X-ray detector, which device comprises an X-ray radiolucent mirror positioned so as to direct the beam emitted from the laser along the central axis of an X-ray beam in the direction of the object, an X-ray opaque target symbol positioned along the central axis between the object and the X-ray detector, a calibration tube having cross-hairs spaced from each other in a direction along said axis, said tube being mounted for movement transverse to said axis, an X-ray imaging device on which images of said cross-hairs are superimposed when an identifiable ray of said X-ray beam is collinear with said axis, and means for directing an optical beam along a line of sight collinear with said axis for targeting structures internal to the object.

11. The method of illumination of a target region on a member embedded in an object which is X-ray transmissive but optically opaque with a beam of light projected along a line of sight through the location of said region, which method comprises the steps of calibrating by locating an identifiable ray of an X-ray beam along a line, aligning said beam of light with said identifiable ray so that said identifiable ray and said light beam are in coaxial relationship along said line along which said identifiable ray is located during said calibrating step, aligning a target which is visible under both visible light and X-ray illumination with said coaxially related ray and light beam to intersect said line, said target aligning said identifiable ray with said target region and said target so that said target region is intersected by said line, and providing illumination along said line with said light beam.

12. The method according to claim 11 wherein said object is a portion of animal anatomy and said member is a bone contained in said portion, and said region is the location of a hole in a rod implanted in said bone, and said method includes the step of making an incision in said portion to said bone along said sighting line.

13. The method according to claim 12 further comprising drilling into said bone along said sighting line to provide a hole for insertion into said drilled hole and said hole in said rod of an element which locks said rod to said bone.

14. A system for illumination of a target region on a member embedded in an object which is X-ray transmissive but optically opaque with a beam of light projected along a line of sight through the location of said region, which system comprises means including X-ray opaque cross-hairs spaced from each other along said line and moveable in orthogonally related directions in a plane transverse to said line for calibrating said system to locate an identifiable ray of said X-ray beam along said line, means for aligning said beam of light with said identifiable ray so that said identifiable ray and light beam are in coaxial relationship along said line, means for aligning a target which is visible under both light and X-ray illumination with said coaxially related ray and beam, said target aligning said X-ray beam with said target region and said target so that said target region is intersected by said line, and means for providing illumination along said line with said light beam.

15. The system according to claim 14 wherein said object is a portion of animal anatomy and said member is a bone contained in said portion, and said region is the location of a hole, a rod implanted in said bone, and said system further comprises means for making an incision in said portion to said bone along said sighting line.

16. The system according to claim 15 wherein said light beam provides means for guiding drilling into said bone along said sighting line to provide a hole for insertion of an element into said holes which locks said rod to said bone.

17. The system according to claim 15 wherein said system includes a laser providing said beam, said laser being of sufficient intensity to make said incision.

18. The system according to claim 15 wherein said laser beam is also of sufficient intensity to drill said hole.

* * * * *